United States Patent [19]

Borden et al.

[11] Patent Number: 5,360,980
[45] Date of Patent: Nov. 1, 1994

[54] STRUCTURE AND METHOD FOR PROVIDING A GAS PURGE FOR A VACUUM PARTICLE SENSOR INSTALLED IN A CORROSIVE OR COATING ENVIRONMENT

[75] Inventors: Peter G. Borden, San Mateo, Calif.; Hoang K. Nguyen, Austin, Tex.; Earl J. Carrasco, Fremont, Calif.

[73] Assignee: High Yield Technology, Sunnyvale, Calif.

[21] Appl. No.: 23,502

[22] Filed: Feb. 26, 1993

[51] Int. Cl.$^5$ ............................................. G01N 15/06
[52] U.S. Cl. ...................................... 250/573; 356/338
[58] Field of Search ............... 250/573, 574, 575, 576; 356/335, 336, 338, 341, 342

[56] References Cited

U.S. PATENT DOCUMENTS

| | | | |
|---|---|---|---|
| 3,986,023 | 10/1976 | Frungel | 250/574 |
| 4,752,131 | 6/1988 | Eisenlauer et al. | 250/573 |
| 5,083,865 | 1/1992 | Kinney et al. | 356/338 |
| 5,153,671 | 10/1992 | Miles | 356/338 |

Primary Examiner—David C. Nelms
Attorney, Agent, or Firm—Skjerven, Morrill, MacPherson, Franklin & Friel

[57] ABSTRACT

A structure and an apparatus are provided for use in particle sensor installed to monitor particle level of a process chamber. The process chamber receives process gas from a supply line and removes gas through an exhaust line. The particle sensor's optical components are prevented from contamination by corrosive or coating species in the effluent from the process, by a gas purge line installed in the particle sensor. The gas purge line allows a flow of gas to purge the optical components at a flux not less than the flux of gas being removed from the process chamber in the exhaust line. The flux out of the particle sensor prevents the undesired species from reaching the optical components of the particle sensor from the sampling area where the particle sensor detects the particle level.

10 Claims, 2 Drawing Sheets

STRUCTURE AND METHOD FOR PROVIDING A GAS PURGE FOR A VACUUM PARTICLE SENSOR INSTALLED IN A CORROSIVE OR COATING ENVIRONMENT

BACKGROUND OF THE INVENTION

1. Field of the Invention

The present invention relates to particle monitoring in a manufacturing process which involves a corrosive or coating agent carried in the process gas. In particular, the present invention relates to particle monitoring in plasma etching or similar processes.

2. Discussion of the Related Art

In a semiconductor fabrication process, plasma etching is often used to selectively remove portions of thin films formed from the surface of a semiconductor wafer. FIG. 1 shows a typical configuration in a process chamber 100 of a plasma etcher. As shown in FIG. 1, a wafer 101 is placed on an electrically grounded platform 102, which also serves as the ground electrode. Placed in close proximity, and substantially parallel to the grounded platform 102, is a "shower head" electrode 103, which applies either a DC (direct current) or an RF (radio frequency) voltage difference across the grounded platform 102 and itself. A plasma, generally represented by reference numeral 104, is created by the applied voltage in the gap above the wafer 101 between grounded platform 102 and "shower head" electrode 103. Process chemicals, such as freon, are carried in an inert gas and injected into the plasma through small holes in shower head electrode 103. These chemicals break down in the plasma, forming reactants that etch material from the surface of wafer 101.

Particles are formed as a byproduct of a plasma etching process. Such particles, when deposited on the surface of wafer 101, results in defects which can reduce the yield of the fabrication process. The control and removal of such particles are therefore critical to reducing the cost of manufacturing. Thus, an optical particle monitor 104 has been developed for use in an environment such as the plasma etching process. An example of an optical particle monitor is disclosed in U.S. Pat. No. 5,132,548, entitled "High Sensitivity Large Detection Area Particle Sensor for Vacuum Applications" to Borden et al, issued Jul. 22, 1992. Optical particle sensor 104 is typically installed in a vacuum exhaust line, such as vacuum exhaust line 105, which carries gas out of the process chamber 100.

Particle sensor 104 is susceptible to the reactants in process chamber 100. In an etching process, reactants such as fluorine compounds and certain polymer byproducts are often created. Fluorine compounds etch and corrode the surfaces of optics in particle sensor 104. In addition, polymer byproducts coat the optic surfaces of particle sensor 104. Such corrosion or coating reduces the performance of optical particle sensor 104. Hence, there is a strong incentive to prevent corrosion or coating on critical optical surfaces of optical particle sensor 104.

In the prior art, various techniques have been used to reduce contamination on the optical surfaces of a particle sensor. One such technique used in an airborne particle sensor is shown in FIG. 2. In FIG. 2, an airborne particle sensor 200 uses filtered air which is combined with a carrier gas stream 204. As shown in FIG. 2, to monitor the particle level in a carrier gas stream 204, carrier gas stream is injected by nozzle 202 through a laser beam 201. Particles carried in carrier gas stream 204 scatter the light in laser beam 201 onto a photodetector 203 mounted in close proximity of laser beam 201. The output signal level of photodetector 203 is a measure of the number of particles in carrier gas stream 204.

In a typical system, laser beam 201 is provided by open cavity laser 205. In open cavity laser 205, one of the mirrors 206 is placed in a position removed from the tube 205a which houses the gas used to generate the laser beam. The gas most often used is a mixture of helium and neon. By placing mirror 206 away from laser tube 205a, open cavity laser 205 creates a portion of the laser beam external to laser tube 205a exposed to the particles to be detected. A problem with using open cavity laser 205 results from particle contamination on the surfaces of the mirror 206 or the window on the laser tube 205a. Particles deposited on these surfaces can scatter enough light from laser beam 201 to make the cavity operate at reduced efficiency. To circumvent this problem, filtered air is injected in the gas line 207 around nozzle 202, so as to provide a jacket of clean air around carrier gas stream 204 carrying the particles. Under this arrangement, particles are prevented from reaching the optics of open cavity laser 205.

However, the technique described above cannot be readily adapted to be used in a low pressure system, since the filtered gas flow must be large, as compared to the flow in carrier gas stream 204. Large filtered gas flow is usually impossible to achieve in the pumping system of the process equipment without seriously affecting the pumping performance. Further, the full diameter of exhaust line 207 of the process equipment is usually required for pumping the process gas, so there is not room remaining for such a shield gas layer.

Thus, it is desirable to provide a means for protecting optics in a particle monitor used in low pressure processes, without seriously affecting the pumping performance of the host processing equipment.

SUMMARY OF THE INVENTION

In accordance with the present invention, a structure and an apparatus are provided for use in a particle sensor installed to monitor the particle level of a process chamber. An example of such a process chamber is that used in a plasma etcher. Typically a process chamber receives process gas from a supply line and removes gas through an exhaust line. The present invention prevents contamination of the particle sensor's optical components by corrosive or coating species in the effluent from the process.

In the present invention, a gas purge line is installed in the particle sensor to allow a flow of gas to purge the optical components at a flux not less than the flux of gas being removed from the process chamber in the exhaust line. The flux out of the particle sensor prevents the undesired species present in the sampling area, where the particle sensor detects the particle level, from reaching the optical components of the particle sensor.

In one embodiment, the optical components includes a beam stop for absorbing a laser beam used in a particle sensor which detects particles by the scattering of light. Preferably, the gas provided in the gas purge line is inert to chemical reactions in said process chamber.

Since many processes use an inert carrier gas, the gas in the purge line can be tapped from a position in the supply line of the inert carrier gas downstream from a valve controlling the flow of the carrier gas. Under this arrangement, when the supply of inert carrier gas is turned off, the flow of gas in the purge line of the particle sensor is automatically turned off, thereby simplifying the necessary control equipment. In one embodiment, a metering valve is provided in the gas purge line to control the flow of gas into the particle sensor.

An advantage of the present invention protects the optics of a particle sensor used in pump lines of vacuum processing equipment.

The present invention is better understood upon consideration of the detailed description below and the accompanying drawings.

DETAILED DESCRIPTION OF THE DRAWINGS

Figure 3:
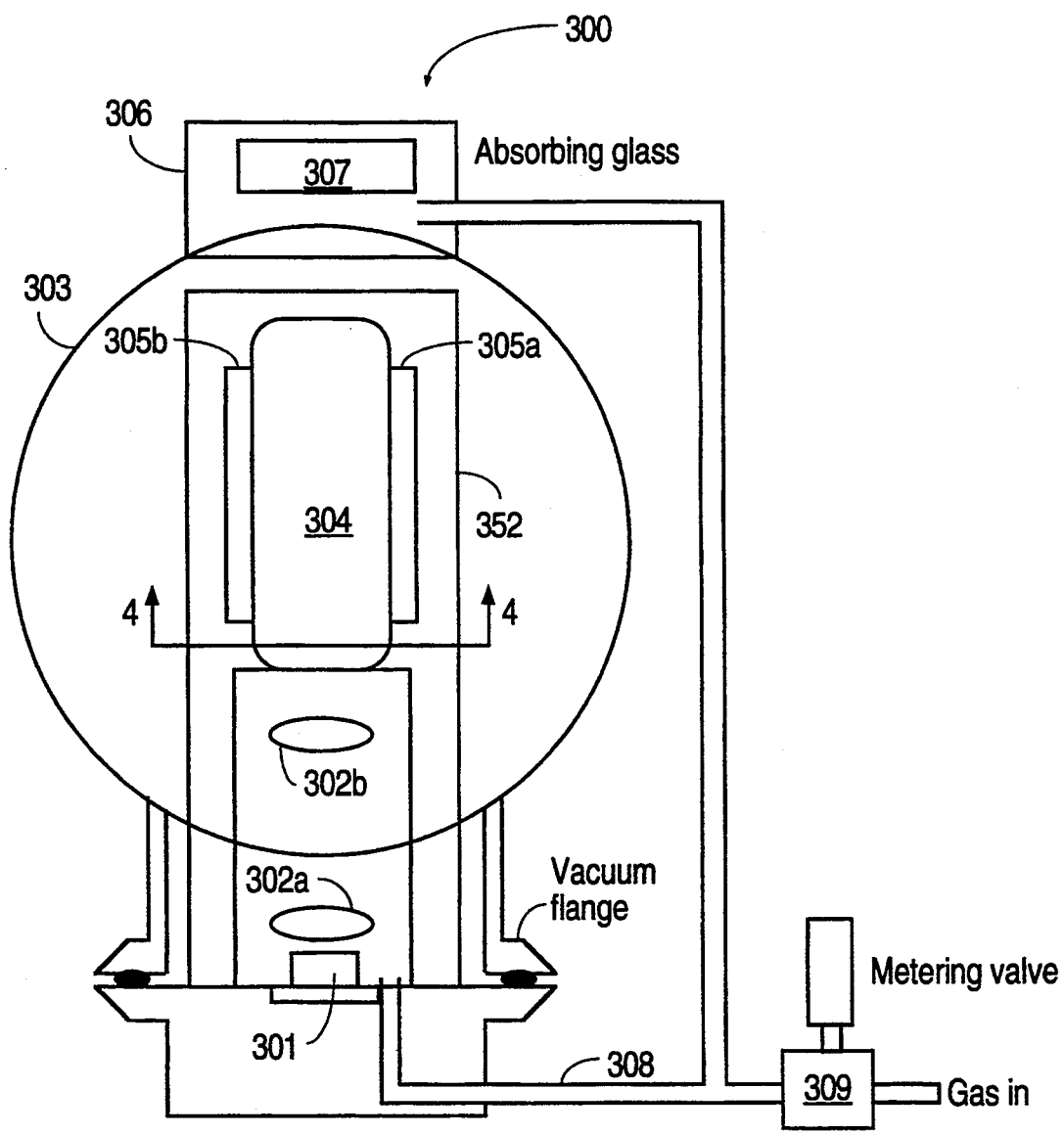
FIG. 3 illustrates a particle monitor 300 of the present invention which provides an inert gas flow through purge line 308 into housing 352 to flush the optical components of particle monitor 300, thereby preventing contamination by the corrosive or coating species created in a plasma etching process.

The present invention is described with the aid of FIG. 3, which shows a particle monitor 300 configured for use in an exhaust line of a process equipment. Particle monitor 300 includes a laser apparatus 301, which provides a laser beam (not shown), and lenses 302a and 302b which collimate and focus the laser beam from laser apparatus 301. The laser beam projects through a sampling area 304 that opens into the exhaust pump line 303 to allow particles carried in pump line 304 to pass through the laser beam. The laser beam terminates at an absorbing glass 307 in beam stop 306. The light scattered by the particles passing through the laser beam is detected by photocells 305a and 305b that are mounted in this embodiment adjacent to the laser beam in the walls surrounding sampling area 304.

Figure 1:
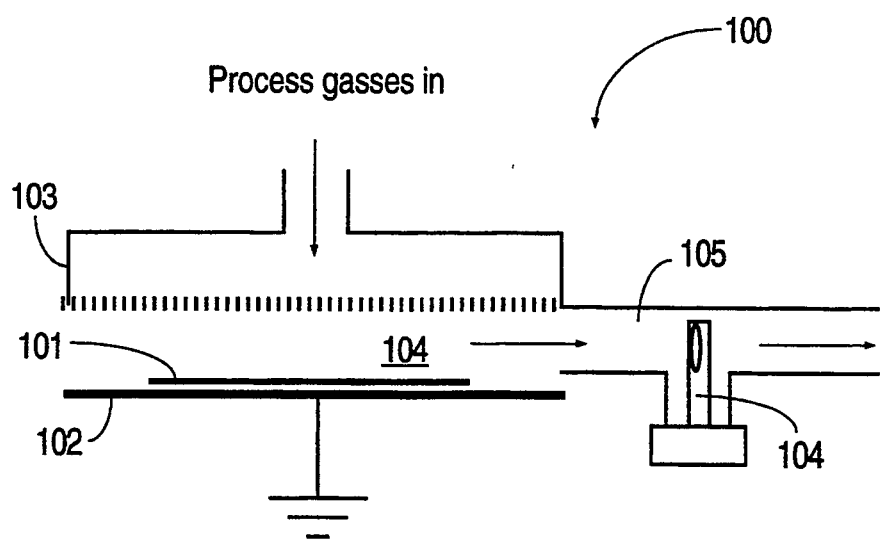
FIG. 1 illustrates a process chamber 100 in a plasma etcher; process chamber 100 has a particle sensor 104 of the prior art installed for detecting particles generated in the plasma.
Figure 2:
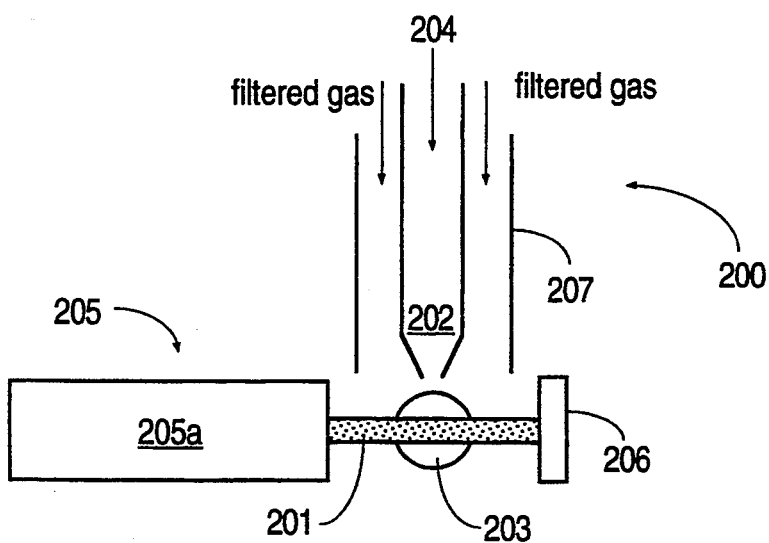
FIG. 2 illustrates a method in the prior art for preventing particle contamination on the optical surfaces of open cavity laser 205, using a protective air sheath to contain particles carried in carrier gas stream 204.
Figure 4:
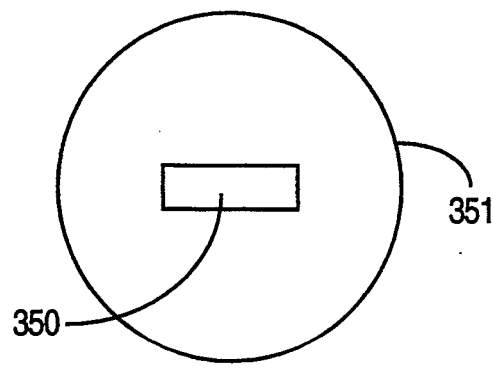
FIG. 4 is a cross section of FIG. 3's particle monitor 300, along a plane defined by the line segment A—A in FIG. 3.

In this embodiment, the laser beam emerges into sampling area 304 through an aperture 350, which is shown in FIG. 4. FIG. 4 is a cross section of particle monitor 300 along the plane defined by the line segment A—A of FIG. 3. As shown in FIG. 4, an aperture 350 is provided to minimize "stray light" at the side of the laser beam. Reference numeral 351 represents generally the external wall of particle sensor 300's housing 352. "Stray light" is the portion of the laser beam which does not stay within the beam and thus may impinge without scattering by the particles onto photocells 305a and 305b. Stray light can be caused, for example, by contamination or coating on the optical components such as the lenses 302a and 302b or beam stop 306. As a practical matter, the performance of a particle sensor, such as particle sensor 300, is sensitive to such stray light. If such stray light is excessive, particle sensor 300 may saturate, thereby rendering it useless in detecting the very small pulses of scattered light created by the small particles passing through the laser beam.

As shown in FIG. 3, to prevent this contamination on the surfaces of the optical components, the present invention provides a small flow of gas through purge line 308 into the portions of sensor housing 352 enclosing the optical components, including lenses 302a, 302b and beam stop 306. The gas in purge line 308 is inert with respect to the chemical processes of the process chamber to prevent undesirable effects on the manufacturing process. This small gas flow in purge line 308 is provided sufficiently strongly, so that there is a net gas flow out of the beam aperture 350 and beam stop 306. In this manner, the optical components inside housing 352 of particle monitor 300 are flushed with clean gas, thereby limiting encroachment of process gas which contains material capable of etching or coating the sensor optics. In this embodiment, the gas flow in purge line 308 is controlled by a commonly available metering valve 309, such as one manufactured by Nupro, Willoughby, Ohio.

As explained above, the gas in purge line 308 is preferably inert with respect to the chemical reactions in the process chamber. In all likelihood, the plasma etching process uses an inert carrier gas, e.g. helium, argon, or, in some cases, nitrogen. In a low pressure process chamber, the carrier gas is turned on during the active part of a process, and turned off when the chamber is "based out," i.e. pumped down to its base pressure. If such an inert gas is used, for convenience, the same gas is preferably used to flush the optical components of the particle monitor. The inert gas for purge line 308 can be drawn at a point in the inert gas supply line downstream from the valve used to turn the inert gas flow on and off during process. In this manner, the sensor is flushed during process when reactive or coating gasses are present, but there is no leak of the flushing gas when the process chamber is being based out.

The flow rate of the gas in purge line 308 is determined by the following procedure. First, the net flux ($flux_{process}$) of process gas down the carrier gas line during process is determined. This is equal to $$flux_{process} = flow_{process} \times \frac{760}{(P_{process} \times Area_{process})}$$

where the total flow ($flow_{process}$) of process gas into the process chamber is given in sccm (standard cubic centimeters per minute), $P_{process}$ is the process pressure in torrs, and $area_{process}$ refers to the cross-section area of the gas line. To prevent contamination of the optical components in the particle monitor, the net flux ($flux_{sensor}$) out of the sensor aperture areas is preferably greater than the flux ($flux_{process}$) of the process gas. In a typical plasma etching process, a pressure ($P_{process}$) of approximately 1 torr and a process gas flow ($flow_{process}$) of 200 sccm are typical. Thus, considering that a pump line often used has a diameter of 40 mm, i.e. a cross section area ($area_{process}$) of 12.56 cm$^2$, the flux ($flux_{process}$) of process gas is approximately 12,100 cc/cm$^2$/sec.

Second, the minimum required gas flow ($flow_{sensor}$) out of the sensor aperture is determined. $Flow_{sensor}$ is given by multiplying the flux ($flux_{sensor}$) of gas out of the sensor aperture by the aperture area ($Area_{sensor}$) of the sensor. Using the above example, assuming that the typical sensor has an aperture of 0.2 cm by 0.5 cm, or 0.1 cm$^2$. Adopting a minimum flux ($flux_{sensor}$) to be equal to the flux ($\text{flux}_{process}$) of the process gas, the minimum flow ($\text{flow}_{sensor}$) required of the gas in the purge line 308 into the sensor is 96 cc/sec at 1 torr, or 0.13 sccm into metering valve 309.

As the process chamber is pumped to base pressure ($P_{base}$), the new total flow ($\text{flow}_{base}$) of process gas down the carrier gas line is given by $$\text{flow}_{base} = \text{flow}_{process} \times \frac{P_{Base}}{P_{process}}$$

Hence, using the same example above, the flow ($\text{flow}_{base}$) of process gas at a typical base pressure of 0.01 torr is 121 cc/sec.

To base pressure can be used to set the flow of gas in particle sensor 300. Metering valve 309 is opened to increase the pressure ($P_{sensor\ base}$) in the purge line 308 at least to the value:

$$P_{sensor\ base} = P_{Base} \times \left(1 + \frac{\text{Flow}_{sensor}}{\text{Flow}_{base}}\right)$$

where $\text{flow}_{sensor}$ is the flow of inert gas out of the sensor aperture, as computed in the second step above. In this example, metering valve 309 should be opened to achieve a new pressure of at least 0.018 Torr. In practice, a slightly higher pressure should be chosen, e.g. 0.03 Torr, to ensure that the flux of gas out of the sensor aperture exceeds the flux of gas in the process exhaust line.

The above detailed description is intended to be illustrate the specific embodiments and is not intended to be limiting. One of ordinary skill will appreciate upon consideration of the above detailed description that numerous variations and modifications are possible within the scope of the present invention. The present invention is defined by the following claims.

What is claimed is:

1. An apparatus for use in conjunction with a process chamber, said process chamber receiving gas from one or more supply lines and removing gas through an exhaust line, said apparatus comprising:

a particle sensor having optical components, said particle sensor having a portion exposed to said exhaust line; and a gas purge line allowing a flow of gas purging said optical components, said flow of gas emerging out of said portion of said particle sensor into said exhaust line and flowing at a flux not less than the flux of gas being removed from said process chamber in said exhaust line.

2. An apparatus as in claim 1, wherein said optical components includes a beam stop.

3. An apparatus as in claim 1, wherein said flow of gas in said particle sensor is inert to chemical reactions in said process chamber.

4. An apparatus as in claim 1, wherein said supply line having a valve for controlling gas received by said process chamber, said flow of gas in said particle sensor being provided by tapping said gas supply line at a position downstream from said valve.

5. An apparatus as in claim 1, wherein said gas purge line is controlled by a metering valve.

6. A method for use to prevent corrosion or coating on the surfaces of optical components in a particle sensor by species from a process chamber, said process chamber receiving gas from a supply line and removing gas through an exhaust line, said apparatus comprising the steps of:

positioning a gas purge line in said particle sensor, such that a flow of gas from said gas purge line purges the surface of said optical components and emerges out of said particle sensor into said exhaust line; and providing said flow of gas in said purge line at a flux not less than the flux of the gas being removed from said process chamber in said exhaust line.

7. A method as in claim 6, wherein said step of providing said flow of gas provides a gas inert to chemical reactions in said process chamber.

8. A method as in claim 6, wherein said optical components of said particle sensor include a beam stop.

9. A method as in claim 6, wherein said step of providing said flow of gas further comprises the step of tapping said gas supply line at a position downstream from a valve controlling the gas flow into said process chamber.

10. A method as in claim 6, further comprising the step of controlling said flow of gas in said gas purge line by a metering valve.

* * * * *